United States Patent
Dong

(10) Patent No.: US 6,242,563 B1
(45) Date of Patent: Jun. 5, 2001

(54) PEPTIDE ANALOGUES

(75) Inventor: Zheng Xin Dong, Holliston, MA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 09/340,878

(22) Filed: Jun. 28, 1999

Related U.S. Application Data

(60) Provisional application No. 60/093,405, filed on Jul. 20, 1998.

(51) Int. Cl.$^7$ .............................. A61K 38/00; C07K 5/00; C07K 7/00
(52) U.S. Cl. .......................... 530/300; 530/324; 514/12; 424/185.1
(58) Field of Search ................................... 530/300, 324; 514/12; 424/185.1

(56) References Cited

U.S. PATENT DOCUMENTS

| | | |
|---|---|---|
| 5,128,242 | 7/1992 | Arimura et al. . |
| 5,208,320 | 5/1993 | Kitada et al. . |
| 5,623,050 | 4/1997 | Kitada et al. . |

FOREIGN PATENT DOCUMENTS

| | | | |
|---|---|---|---|
| 0 529 487 A3 | 3/1993 | (EP) . | |
| WO 96/09064 | 3/1996 | (WO) . | |
| 9609064 * | 3/1996 | (WO) | .............................. A61K/38/16 |

OTHER PUBLICATIONS

Arimura et al., Frontiers in Neuroendocrinology, vol. 16, pp. 53–88, 1995.

Christophe, J., Biochimica et Biophysica Acta., 1154, pp. 183–199, 1993.

Arimura, A., Regulatory Peptides, 37:287–303, 1992.

Robberecht, P., et al., Molecular Pharmacology, 42:347–355, 1992.

Somogyvari–Vigh, A., et al., Dept. of Medicine and U.S.–Japan Biomed. Res. Labs., Tulane Univ. Medical Center, Belle Chasse, LA, USA.

Robberecht et al., *Molecular Pharmacology*, vol. 42, 1992, pp. 347–355.*

* cited by examiner

*Primary Examiner*—Avis M. Davenport
(74) *Attorney, Agent, or Firm*—Alan F. Feeney; Brian R. Morrill; Fish & Richardson

(57) ABSTRACT

The present invention is directed to novel analogues of PACAP (Pituitary Adenylate Cyclase Activating Polypeptide) as described in the specification, which are agonists of the PACAP receptor and as such are useful in treating cerebrovascular ischemia, male impotence, motor neuron disease, neuropathy, pain, depression, anxiety disorders, brain trauma, memory impairments, dementia, cognitive disorder, central nervous system diseases (such as Parkinson's disease, Alzheimer's disease), migraine, neurodegenerative diseases, ischemic heart disease, myocardial infarction, fibrosis, restenosis, diabetes mellitus, muscle disease, gastric ulcer, stroke, atherosclerosis, hypertension, septic shock, thrombosis, retina disease, cardiovascular disease, renal failure and cardiac failure and the prevention of neuronal cell death in a mammal. This invention is also directed to pharmaceutical compositions useful therefor.

22 Claims, No Drawings

SEQUENCE LISTING

<160> NUMBER OF SEQ ID NOS: 1

<210> SEQ ID NO: 1
<211> LENGTH: 38
<212> TYPE: PRT
<213> ORGANISM: Artificial Sequence
<220> FEATURE:
<223> OTHER INFORMATION: Description of Artificial Sequence: Formula
      peptide
<221> NAME/KEY: MOD_RES
<222> LOCATION: (1)
<223> OTHER INFORMATION: His or Pal
<221> NAME/KEY: MOD_RES
<222> LOCATION: (2)
<223> OTHER INFORMATION: Ser, Thr or hSer
<221> NAME/KEY: MOD_RES
<222> LOCATION: (3)
<223> OTHER INFORMATION: Asp or Glu
<221> NAME/KEY: MOD_RES
<222> LOCATION: (4)
<223> OTHER INFORMATION: Gly, B-Ala, Gaba, Ava, Aib, or Acc
<221> NAME/KEY: MOD_RES
<222> LOCATION: (5)
<223> OTHER INFORMATION: Ile, Leu, Cha, Nle, Val, Tle, Abu, Aib, Acc or
      Nva
<221> NAME/KEY: MOD_RES
<222> LOCATION: (6)
<223> OTHER INFORMATION: Phe, p-X-Phe (wherein X = OH, a halogen or
      CH3), B-Nal, Cha, Tyr, Trp, Acc or Aib
<221> NAME/KEY: MOD_RES
<222> LOCATION: (7)
<223> OTHER INFORMATION: Thr, Ser or Val
<221> NAME/KEY: MOD_RES
<222> LOCATION: (8)
<223> OTHER INFORMATION: Asp or Glu
<221> NAME/KEY: MOD_RES
<222> LOCATION: (9)
<223> OTHER INFORMATION: Ser, Thr or hSer
<221> NAME/KEY: MOD_RES
<222> LOCATION: (10)
<223> OTHER INFORMATION: Tyr, p-X-Phe (wherein X = OH, a halogen or
      CH3), Phe, Amp, B-Nal, Trp or Acc
<221> NAME/KEY: MOD_RES
<222> LOCATION: (11)
<223> OTHER INFORMATION: Ser, Thr or hSer
<221> NAME/KEY: MOD_RES
<222> LOCATION: (12)
<223> OTHER INFORMATION: Arg, Lys, Orn, or hArg
<221> NAME/KEY: MOD_RES
<222> LOCATION: (13)
<223> OTHER INFORMATION: Tyr, p-X-Phe (wherein X = OH, a halogen or
      CH3), Phe, Amp, B-Nal, Trp or Acc
<221> NAME/KEY: MOD_RES
<222> LOCATION: (14)
<223> OTHER INFORMATION: Arg, Lys, Orn or hArg
<221> NAME/KEY: MOD_RES
<222> LOCATION: (15)
<223> OTHER INFORMATION: Arg, Lys, Orn or hArg
<221> NAME/KEY: MOD_RES
<222> LOCATION: (16)
<223> OTHER INFORMATION: Gln, Glu, Asp or Asn
<221> NAME/KEY: MOD_RES
<222> LOCATION: (17)
<223> OTHER INFORMATION: Met, Leu, Nle, Abu, Tle, Val, Ile, Cha, Ala,
      Aib, Acc or Nva
<221> NAME/KEY: MOD_RES
<222> LOCATION: (18)
<223> OTHER INFORMATION: Ala, Aib or Acc
<221> NAME/KEY: MOD_RES
<222> LOCATION: (19)
<223> OTHER INFORMATION: Val, Leu, Ile, Ala, Abu, Tle, Cha, Aib, Acc,
      Nle or Nva
<221> NAME/KEY: MOD_RES
<222> LOCATION: (20)
<223> OTHER INFORMATION: Lys, Arg, Orn, hArg or is deleted
<221> NAME/KEY: MOD_RES

```
<222> LOCATION: (21)
<223> OTHER INFORMATION: Lys, Arg, Orn, hArg or is deleted
<221> NAME/KEY: MOD_RES
<222> LOCATION: (22)
<223> OTHER INFORMATION: Tyr, p-X-Phe (wherein X = OH, a halogen or
      CH3), Phe, Amp, B-Nal, Trp, Acc or is deleted
<221> NAME/KEY: MOD_RES
<222> LOCATION: (23)
<223> OTHER INFORMATION: Leu, Ile, Nle, Tle, Met, Val, Ala, Aib, Acc,
      Cha, Phe, p-X-Phe (wherein X = OH, a halogen or CH3),Abu, Nva or
      is deleted
<221> NAME/KEY: MOD_RES
<222> LOCATION: (24)
<223> OTHER INFORMATION: Ala, Aib, Val, Abu, Acc, Ile, Leu, Nle, Tle,
      Nva or is deleted
<221> NAME/KEY: MOD_RES
<222> LOCATION: (25)
<223> OTHER INFORMATION: Ala, Glu, Aib, Val, Abu, Acc, Ile, Leu, Nle,
      Nva Tle or is deleted
<221> NAME/KEY: MOD_RES
<222> LOCATION: (26)
<223> OTHER INFORMATION: Val, Leu, Ile, Ala, Abu, Tle, Cha, Aib, Acc,
      Nva, Nle or is deleted
<221> NAME/KEY: MOD_RES
<222> LOCATION: (27)
<223> OTHER INFORMATION: Leu, Ile, Nle, Tle, Met, Val, Ala, Aib, Acc,
      Nva, Cha, Phe, p-X-Phe (wherein X = OH, a halogen or CH3), Abu or
      is deleted
<221> NAME/KEY: MOD_RES
<222> LOCATION: (28)
<223> OTHER INFORMATION: Gly, Aib, Acc, B-Ala, Gaba, Ava or is deleted
<221> NAME/KEY: MOD_RES
<222> LOCATION: (29)
<223> OTHER INFORMATION: Lys, Arg, Orn, hArg or is deleted
<221> NAME/KEY: MOD_RES
<222> LOCATION: (30)
<223> OTHER INFORMATION: Lys, Arg, Orn, hArg or is deleted
<221> NAME/KEY: MOD_RES
<222> LOCATION: (31)
<223> OTHER INFORMATION: Tyr, p-X-Phe (wherein X = OH, a halogen or
      CH3), Phe, Amp, B-Nal, Trp, Acc or is deleted
<221> NAME/KEY: MOD_RES
<222> LOCATION: (32)
<223> OTHER INFORMATION: Lys, Arg, Orn, hArg or is deleted
<221> NAME/KEY: MOD_RES
<222> LOCATION: (33)
<223> OTHER INFORMATION: Gln, Asn, Glu, Asp or  is deleted
<221> NAME/KEY: MOD_RES
<222> LOCATION: (34)
<223> OTHER INFORMATION: Lys, Arg, Orn, hArg or is deleted
<221> NAME/KEY: MOD_RES
<222> LOCATION: (35)
<223> OTHER INFORMATION: Val, Leu, Ile, Ala, Abu, Tle, Cha, Aib, Nva,
      Acc, Nle or is deleted
<221> NAME/KEY: MOD_RES
<222> LOCATION: (36)
<223> OTHER INFORMATION: Lys, Arg, Orn, hArg or is deleted
<221> NAME/KEY: MOD_RES
<222> LOCATION: (37)
<223> OTHER INFORMATION: Asn, Gln, Asp, Glu, Ala, Aib, Acc or is deleted
<221> NAME/KEY: MOD_RES
<222> LOCATION: (38)
<223> OTHER INFORMATION: Lys, Arg, Orn, hArg or is deleted

<400> SEQUENCE: 1

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
              20                  25                  30

Xaa Xaa Xaa Xaa Xaa Xaa
          35
```

PEPTIDE ANALOGUES

CROSS-REFERENCE TO RELATED APPLICATIONS

This is a non-provisional application claiming the benefit of co-pending U.S. provisional application, Application No. 60/093,405, filed Jul. 20, 1998.

BACKGROUND OF THE INVENTION

The present invention is directed to novel analogues of PACAP (Pituitary Adenylate Cyclase Activating Polypeptide) and the use thereof for treating the conditions and or diseases as described herein.

A review of PACAP and its physiological function is summarized in Christophe, J., Biochimica et Biophysica Acta, 1154, 183–199 (1993), as follows.

PACAP a member of a super family that already includes several regulatory peptides, e.g., VIP, PHI, PHV, secretin, helodermin, helospectin I and II, glucagon, GIP and GRF. This biologically active neuropeptide exists in two amidated forms: PACAP(1–38)-$NH_2$ (PACAP-38) and PACAP (1–27)-$NH_2$ (PACAP-27). The deduced amino acid sequence of PACAP-38 in man (Kimura, C., et al., Biochem. Biophys. Res. Commun., 166, 81–89, (1990)) and rat (Ogi, K., et al., Biochem. Biophys. Res. Commun., 173, 1271–1279, (1990)) is identical to that of the isolated ovine PACAP-38.

At least two classes of PACAP receptors have been described in mammalian tissues and cell lines: type I PACAP-preferring receptors and type II receptors which bind PACAP-27, PACAP-38 and VIP (vasoactive intestinal peptide) (Cauvin, A., et al., Peptides, 11, 773–777 (1990) and Shivers, B. D., et al., Endocrinology, 128, 3055–3065 (1991)). In addition, the first type is capable to display two subtypes, and the second type can be tentatively divided into three subtypes.

Type I is highly selective in that it recognizes PACAP-27 and PACAP-38 much more potently than VIP. PACAP-38 and PACAP-27 can thereafter activate adenylate cyclase with the same high potency and efficacy. Type I receptors may, however, be present as two coexisting subtypes (or states) based on radioligand binding. In rat brain membranes (Cauvin, A., et al., Regul. Pept. 35, 161–173, (1991)), the PACAP-A subtype exhibits hardly any preference for PACAP-38 over PACAP-27, whereas the PACAP-B subtype recognizes PACAP-38 with high affinity and PACAP-27 with low affinity.

The type II receptor is the classical VIP receptor. Based on binding affinity and adenylate cyclase activation, it now appears that the type II receptor is non-selective since it shows similar high affinity for PACAP-27, PACAP-38 and VIP.

A relatively comprehensive spectrum of pharmacological activities has already been established for the physiological roles of PACAP.

Concerning the hypothalamo-pituitary axis, PACAP reduces food intake in mice and raises plasma arginine vasopressin in rat, probably through PACAP-ir (ir= immunoreactive) neurons in paraventricular and supraoptic nuclei projecting to the neurohypophysis. PACAP originating in the hypothalamus may also be transported to the anterior pituitary through portal vessels. Data on the antehypophysis suggest a role on i.a. reproduction and growth. PACAP stimulates adenylate cyclase and increases [$Ca^{2+}$] in gonadotropes, somatotropes, and folliculostellate cells. It elevates the secretion of α-MSH from melanotropes, and that of interleukin-6 from pituitary folliculo-stellate cells. PACAP potentiates the effects of LHRH (or GnRH, gonadotropin releasing hormone) on LH (lutenizing hormone) and FSH secretion. More clearly perhaps, PACAP increases the synthesis of LH, GH (growth hormone), PRL (prolactin) and ACTH after 1–2 days. In human pathology, PACAP-27 and PACAP-38 stimulate adenylate cyclase activity in membranes from "null", gonadotropin-, GH-, and ACTH-producing pituitary adenomas.

In brain, and outside the hypothalamus, PACAP stimulates the synthesis of melatonin from pinealocytes and may play a role in the integration of visual inputs and in memory. The widespread distribution of specific type I PACAP receptors contrasts with the more focused localization of type II VIP-PACAP receptors. Type I receptors in the rabbit eye may contribute to the physiology of the retina and choroid. In general, the neuronal increases in cAMP and $Ca^{2+}$ could contribute to early brain development, repair, and modification of circuitry, with the help of neurotropic factors from astrocytes that are also stimulated by PACAP.

Type I receptors represent a minority (20%) as compared to type II receptors in rat liver. PACAP directly relaxes the digestive tract motility via activation of apamin-sensitive calcium-activated $K^+$ channels and is an anion secretory neuropeptide on rat jejunal mucosa, possibly through submucous neurons. PACAP contracts the gallbladder in conscious dog by a preganglionic mechanism. In vivo it increases amylase secretion via a cholinergic mechanism in dog and glucagon release in mice.

PACAP provokes the hypersecretion and synthesis of catecholamines from the rat adrenal and facilitates mitosis, neurite genesis, and survival of cultured rat sympathetic neuroblasts. A bolus i.v. injection of PACAP induces a biphasic change in blood pressure (decrease followed by increase) that is accompanied by a biphasic change in systemic vascular resistance. The pressor response is due to the release of catecholamines from the adrenal gland. The relaxant action of PACAP in isolated rabbit precontracted aortic rings is 100-fold more potent than VIP, surprisingly durable, and endothelium-independent. PACAP is also a potent microvasodilator in human skin and here its action is long lasting again. PACAP-38 causes an increase in beating rate in neonatal rat cardiomyocytes and stimulates adenylate cyclase in purified sarcolemmal membranes from porcine and canine ventricles. PACAP relaxes the airway and vascular smooth muscle in guinea-pig, rat and cat lung. PACAP-ir is abundant in the rat testis and type I receptors in spermatozoa may play a role in sperm motility.

In addition, PACAP may intervene in ontogenetic processes in the nervous system and modulate mitogenesis and differentiation (e.g., neurite outgrowth) in several cell lines where maligancy is sometimes at the origin of type I receptor emergence.

Therefore, there is a keen interest to find analogues of PACAP which are more active than PACAP-27 and/or PACAP-38 and/or which possess a longer half-life in a patient.

U.S. Pat. No. 5,208,320 discloses certain peptides that produce c-AMP activity. Robberecht, P., et al., Molecular Pharmacology 42:347–355, (1992) discloses a series of PACAP-27 and PACAP-38 analogues. PCT publication no. WO 96/09064 discloses a series of PACAP analogues for use in preventing or treating brain damage.

SUMMARY OF THE INVENTION

This invention is directed to a peptide of formula (I),

$$-A^{12}-A^{13}-A^{14}-A^{15}-A^{16}-A^{17}-A^{18}-A^{19}-A^{20}-A^{21}-A^{22}-A^{23}$$

$$-A^{24}-A^{25}-A^{26}-A^{27}-A^{28}-A^{29}-A^{30}-A^{31}-A^{32}-A^{33}-A^{34}-A^{35}$$

$$-A^{36}-A^{37}-A^{38}-R^3 \quad (I),$$

or a pharmaceutically acceptable salt thereof, wherein, $A^1$ is His or Pal;

$A^2$ is Ser, Thr or hSer;

$A^3$ is Asp or Glu;

$A^4$ is Gly, β-Ala, Gaba, Ava, Aib, Acc or HN—$(CH_2)_m$—C(O);

$A^5$ is Ile, Leu, Cha, Nle, Val, Tle, Abu, Aib, Acc or Nva;

$A^6$ is Phe, p-X-Phe, β-Nal, Cha, Tyr, Trp, Acc or Aib;

$A^7$ is Thr, Ser or Val;

$A^8$ is Asp or Glu;

$A^9$ is Ser, Thr or hSer;

$A^{10}$ is Tyr, p-X-Phe, Phe, Amp, β-Nal, Trp or Acc;

$A^{11}$ is Ser, Thr or hSer;

$A^{12}$, $A^{14}$ and $A^{15}$ are each independently selected from the group consisting of Arg, Lys, Orn, hArg and HN—CH$((CH_2)_n$—NH—$R^4)$—C(O);

$A^{13}$ is Tyr, p-X-Phe, Phe, Amp, β-Nal, Trp or Acc;

$A^{16}$ is Gln, Glu, Asp or Asn;

$A^{17}$ is Met, Leu, Nle, Abu, Tle, Val, Ile, Cha, Ala, Aib, Acc or Nva;

$A^{18}$ is Ala, Aib or Acc;

$A^{19}$ is Val, Leu, Ile, Ala, Abu, Tle, Cha, Aib, Acc, Nle or Nva;

$A^{20}$, $A^{21}$, $A^{29}$, $A^{30}$, $A^{32}$, $A^{34}$, $A^{36}$, and $A^{38}$ are each independently selected from the group consisting of Lys, Arg, Orn, hArg and HN—CH$((CH_2)_n$—NH—$R^4)$—C(O) or is deleted;

$A^{22}$ is Tyr, p-X-Phe, Phe, Amp, β-Nal, Trp, Acc or is deleted;

$A^{23}$ is Leu, Ile, Nle, Tle, Met, Val, Ala, Aib, Acc, Cha, Phe, p-X-Phe, Abu, Nva or is deleted;

$A^{24}$ is Ala, Aib, Val, Abu, Acc, Ile, Leu, Nle, Tle, Nva or is deleted;

$A^{25}$ is Ala, Glu, Aib, Val, Abu, Acc, Ile, Leu, Nle, Nva, Tle or is deleted;

$A^{26}$ is Val, Leu, Ile, Ala, Abu, Tle, Cha, Aib, Acc, Nva, Nle or is deleted;

$A^{27}$ is Leu, Ile, Nle, Tle, Met, Val, Ala, Aib, Acc, Nva, Cha, Phe, p-X-Phe, Abu or is deleted;

$A^{28}$ is Gly, Aib, Acc, β-Ala, Gaba, Ava, HN—$(CH_2)_m$—C(O) or is deleted;

$A^{31}$ is Tyr, p-X-Phe, Phe, Amp, β-Nal, Trp, Acc or is deleted;

$A^{33}$ is Gln, Asn, Glu, Asp or is deleted;

$A^{35}$ is Val, Leu, Ile, Ala, Abu, Tle, Cha, Aib, Nva, Acc, Nle or is deleted;

$A^{37}$ is Asn, Gln, Asp, Glu, Ala, Aib, Acc or is deleted;

$R^1$ and $R^2$ are each independently selected from the group consisting of H, $(C_1-C_{30})$alkyl, $(C_2-C_{30})$ alkenyl, phenyl-$(C_1-C_{30})$alkyl, naphthyl-$(C_1-C_{30})$alkyl, hydroxy-$(C_1-C_{30})$alkyl, hydroxy-$(C_2-C_{30})$alkenyl, hydroxy-phenyl-$(C_1-C_{30})$alkyl or hydroxy-naphthyl-$(C_1-C_{30})$alkyl; or one of $R^1$ or $R^2$ is $COX^2$ where $X^2$ is $(C_1-C_{30})$alkyl, $(C_2-C_{30})$alkenyl, phenyl-$(C_1-C_{30})$alkyl, naphthyl-$(C_1-C_{30})$alkyl, hydroxy-$(C_1-C_{30})$alkyl, hydroxy-$(C_2-C_{30})$alkenyl, hydroxy-phenyl-$(C_1-C_{30})$alkyl or hydroxy-naphthyl-$(C_1-C_{30})$alkyl;

$R^3$ is OH, $NH_2$, $(C_1-C_{30})$alkoxy or NH—Y—$CH_2$—Z, where Y is a $(C_1-C_{30})$ hydrocarbon moiety and Z is $CO_2H$ or $CONH_2$;

where X for each occurrence is independently selected from the group consisting of OH, $OCH_3$, F, Cl, Br and $CH_3$;

m for each occurrence is independently an integer from 5–10;

n for each occurrence is independently an integer from 1–5; and $R^4$ for each occurrence is independently $(C_1-C_{30})$alkyl, $(C_1-C_{30})$acyl or —C((NH)($NH_2$)).

A preferred group of peptides of formula (I), denoted Group A, are those peptides wherein at least one of $A^5$, $A^{17}$, $A^{18}$, $A^{19}$, $A^{23}$, $A^{27}$, $A^{28}$ and $A^{35}$ is Acc, or a pharmaceutically acceptable salt thereof.

A preferred group of the Group A peptides, denoted Group B, are those peptides wherein at least one of $A^5$, $A^{17}$, $A^{18}$, $A^{19}$, $A^{23}$, $A^{27}$, $A^{28}$ and $A^{35}$ is A6c or A5c, or a pharmaceutically acceptable salt thereof.

A preferred group of the Group B peptides, denoted Group C, are those peptides wherein at least one of $A^5$, $A^{18}$ and $A^{19}$ is A5c, or a pharmaceutically acceptable salt thereof.

A preferred group of the Group B peptides, denoted Group D, are those peptides wherein at least one of $A^{17}$, $A^{19}$, $A^{23}$, $A^{27}$, $A^{28}$ and $A^{35}$ is A6c, or a pharmaceutically acceptable salt thereof.

A preferred group of the peptides of formula (I), denoted Group E, are those peptides wherein at least one of $A^4$ and $A^{28}$ is β-Ala, Gaba or Ava, or a pharmaceutically acceptable salt thereof.

A preferred group of the Group E peptides, denoted Group F, are those peptides wherein at least one of $A^4$ and $A^{28}$ is β-Ala; or a pharmaceutically acceptable salt thereof.

A preferred group of the Group E peptides, denoted Group G, are those peptides wherein $A^{28}$ is Gaba or Ava, or a pharmaceutically acceptable salt thereof.

A preferred group of the peptides of formula (I), denoted Group H, are those peptides wherein at least one of $A^{18}$, $A^{24}$, $A^{25}$ and $A^{37}$ is Aib, or a pharmaceutically acceptable salt thereof.

A preferred group of the peptides of formula (I), denoted Group I, are those peptides wherein at least one of $A^{16}$, $A^{25}$ and $A^{33}$ is Glu, or a pharmaceutically acceptable salt thereof.

A preferred group of the peptides of formula (I), denoted Group J, are those peptides wherein $A^{38}$ is Lys-N-ε-octadecanoyl.

A preferred group of the Group C peptides, denoted Group K, are [A5c$^5$]hPACAP(1–38)$NH_2$, [A5c$^{19}$]hPACAP(1–38)$NH_2$, [Leu$^{17}$, A5c$^{19}$]hPACAP(1–38)$NH_2$, [Nle$^{17}$, A5c$^{19}$]hPACAP(1–38)$NH_2$, [N-α-octadecanoyl-His$^1$, A5c$^{19}$]hPACAP(1–38)$NH_2$, [A5c$^{19}$, (Lys-N-$_{68}$-octadecanoyl)$^{38}$]hPACAP(1–38)$NH_2$ and [A5c$^{18}$]hPACAP(1–38)$NH_2$.

A preferred group of the Group D peptides, denoted Group L, are [A6c$^{23,27}$]hPACAP(1–38)$NH_2$, [A6c$^{17}$]hPACAP(1–38)$NH_2$, [A6c$^{19,23}$]hPACAP(1–38)$NH_2$, [A6c$^{23}$]hPACAP(1–38)$NH_2$, [A6c$^{27}$]hPACAP(1–38)$NH_2$, [A6c$^{28}$]hPACAP(1–38)$NH_2$, [A6c$^{35}$]hPACAP(1–38)$NH_2$ and [A6c$^{19}$]hPACAP(1–38)$NH_2$.

A preferred group of the Group F peptides, denoted Group M, are [β-Ala$^{28}$]hPACAP(1–38)$NH_2$, [A5c$^{19}$, β-Ala$^{28}$]hPACAP(1–38)$NH_2$ and [β-Ala$^4$]hPACAP(1–38)$NH_2$.

A preferred group of the Group G peptides, denoted Group N, are [Gaba$^{28}$]hPACAP(1–38)$NH_2$ and [Ava$^{28}$]hPACAP(1–38)$NH_2$.

A preferred group of the Group H peptides, denoted Group O, are [Aib$^{37}$]hPACAP(1–38)NH$_2$, [Aib$^{24}$, A6c$^{27}$]hPACAP(1–38)NH$_2$, [Aib$^{18}$, A6c$^{23}$]hPACAP(1–38)NH$_2$, [Aib$^{18,25}$, A6c$^{23}$]hPACAP(1–38)NH$_2$ and [A6c$^{23}$, Aib$^{25}$]hPACAP(1–38)NH$_2$.

A preferred group of the Group I peptides, denoted Group P, are [Glu$^{16}$]hPACAP(1–38)NH$_2$, [Glu$^{33}$]hPACAP(1–38)NH$_2$, [Aib$^{24}$, Glu$^{25}$]hPACAP(1–38)NH$_2$ and [Glu$^{33}$, A6c$^{35}$]hPACAP(1–38)NH$_2$, In another aspect, this invention is directed to a pharmaceutical composition comprising an effective amount of a peptide of formula (I) as described hereinabove or a pharmaceutically acceptable salt thereof and a pharmaceutically acceptable carrier.

In yet another aspect, this invention is directed to a method of treating cerebrovascular ischemia, male impotence, motor neuron disease, neuropathy, pain, depression, anxiety disorders, brain trauma, memory impairments, dementia, cognitive disorder, central nervous system diseases, migraine, neurodegenerative diseases, ischemic heart disease, myocardial infarction, fibrosis, restenosis, diabetes mellitus, muscle disease, gastric ulcer, stroke, atherosclerosis, hypertension, septic shock, thrombosis, retina disease, cardiovascular disease, renal failure or cardiac failure or preventing neuronal cell death in a mammal in need thereof, which comprises administering to said mammal an effective amount of a peptide of formula (I) as described hereinabove or a pharmaceutically acceptable salt thereof.

A preferred method of the immediately foregoing method is where the central nervous system disease treated is Parkinson's disease or Alzheimer's disease.

In still another aspect, this invention provides a method of binding PACAP receptors in a mammal in need thereof, which comprises administering to said mammal an effective amount of a peptide of formula (I) or a pharmaceutically acceptable salt thereof.

In a further aspect, this invention provides a method of eliciting an agonist effect from a PACAP receptor in a mammal in need thereof, which comprises administering to said mammal an effective amount of a peptide of formula (I) or a pharmaceutically acceptable salt thereof.

DETAILED DESCRIPTION OF THE INVENTION

With the exception of the N-terminal amino acid, all abbreviations (e.g., Ala for A$_1$) of amino acids in this disclosure stand for the structure of —NH—CH(R)—CO—, wherein R in the immediately foregoing formula is the side chain of an amino acid (e.g., CH$_3$ for Ala). For the N-terminal amino acid, the abbreviation stands for the structure of (R$^1$R$^2$)—N—CH(R)—CO—, wherein R is a side chain of an amino acid and R$^1$ and R$^2$ are as defined above.

The following are abbreviations of certain α-amino acids: β-Nal=β-(2-naphthyl)alanine; Nle=norleucine; Cha=cyclohexylalanine; Nva=norvaline; Amp=4-aminophenylalanine; Pal=β-(3-pyridinyl)alanine; Aib=α-aminoisobutyric acid; hSer=homoserine; β-Ala=β-alanine; Gaba=γ-aminobutyric acid; Ava=5-aminovaleric acid; and Abu=α-aminobutyric acid.

What is meant by Acc is the general abbreviation for a cycloalkyl amino acid which includes but is not limited to: 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexane-carboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c). The terms hydroxyalkyl, hydroxyphenylalkyl, and hydroxynaphthylalkyl is intended to mean that there can be one or more hydroxy substituents on the alkyl group and/or the phenyl and naphthyl group. COX$^2$ stands for —(C=O)X$^2$, examples of —(C=O)X$^2$ include acetyl and phenylpropionyl. What is meant by "(C$_1$–C$_{30}$) hydrocarbon moiety" is an alkyl group, an alkenyl group or an alkynyl group, where in the instance of an alkenyl or alkynyl group it is understood that a minimum of two carbons must be present.

A peptide of this invention is also denoted herein by another format, e.g., [β-Ala$^{28}$]hPACAP(1–38)NH$_2$, with the substituted amino acids from the natural sequence placed between the set of brackets (e.g., β-Ala$^{28}$ for Gly$^{28}$ in hPACAP). The abbreviation hPACAP stands for human PACAP. The numbers between the parentheses refer to the number of amino acids present in the peptide (e.g., hPACAP (1–38) is amino acids 1 through 38 of the peptide sequence for human PACAP). The sequence for hPACAP(1–38) is listed in Christophe, J., et al., *Biochimica et Biophysica Acta*, 1154, 183–199, (1993). The designation "NH$_2$" in PACAP (1–38)NH$_2$ indicates that the C-terminus of the peptide is amidated. PACAP(1–38), on the other hand, has a free acid C-terminus.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

As is well known to those skilled in the art, the known and potential uses of PACAP is varied and multitudinous [See Arimura, A., *Regulatory Peptides*, 37, (1992), 287–303; Christophe, J., *Biochimica et Biophysica Acta*, 1154, (1993), 183–199; Arimura, A. and Shioda, S., *Frontiers in Neuroendocrinology*, 16, 53–88 (1995)]. Thus, the administration of the compounds of this invention for purposes of eliciting an agonist effect can have the same effects and uses as PACAP itself. These varied uses of PACAP may be summarized as follows: cerebrovascular ischemia, Alzheimer's disease, male impotence, motor neuron disease, neuropathy, pain, depression, anxiety disorders, brain trauma, memory impairments, dementia, cognitive disorder, central nervous system diseases (such as Parkinson's disease, Alzheimer's disease), migraine, neurodegenerative diseases, prevention of neuronal cell death, ischemic heart disease, myocardial infarction, fibrosis, restenosis, diabetes mellitus, muscle disease, gastric ulcer, stroke, atherosclerosis, hypertension, septic shock, thrombosis, retina disease, cardiovascular disease, renal failure and cardiac failure.

Accordingly, the present invention includes within its scope pharmaceutical compositions comprising, as an active ingredient, at least one of the compounds of Formula I in association with a pharmaceutically acceptable carrier.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of 0.00001 to 200 mg/kg/day, preferably 0.001 to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

In vitro assays: A compound of the instant invention can be tested for its ability to bind to PACAP type I and type II receptors according to the following procedure.

Cell Culture: Rat AR42J pancreas cells (ATCC, Rockville, Md.), expressing the PACAP-I receptor, were cultured in Dulbecco's modified Eagle's medium (DMEM) containing 10% fetal calf serum, and maintained at 37° C. in a humidified atmosphere of 5% $CO_2$/95% air.

Animals: Male rats (Taconic, Germantown, N.Y.) were sacrificed by decapitation and the livers were obtained and used as the source of the PACAP-II receptor.

Radioligand Binding: Membranes were prepared for radioligand binding studies by homogenization of the AR42J cells (for PACAP-I receptor) or rat liver (for PACAP-II receptor) in 20 ml of ice-cold 50 mM Tris-HCl with a Brinkman Polytron (Brinkman, Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM [$^{125}$I]PACAP-27 (2200 Ci/mmol, New England Nuclear, Boston, Mass.), with and without 0.05 ml of unlabeled competing test compound. After a 40 min incubation (25° C.), the bound [$^{125}$I]PACAP-27 was separated from the free [$^{125}$I]PACAP-27 by rapid filtration through GF/B filters (Brandel, Gaithersburg, Md.), which had been previously soaked in 0.3% polyethyleneimine. The filters were then washed three times with 5-ml aliquots of ice-cold 50 mM Tris-HCl, and the bound radioactivity trapped upon the filters was counted by gamma spectrometry (Wallac LKB, Gaithersburg, Md.). Specific binding to either the Type I receptor or the Type II receptor was defined as the total [$^{125}$I]PACAP-27 bound minus that bound in the presence of 1000 nM PACAP-27 (Bachem, Torrence, Calif.).

Synthesis

The peptides of the present invention can be prepared by standard solid phase synthesis. See, e.g., Stewart, J. M., et al., Solid Phase Synthesis (Pierce Chemical Co., 2d ed. 1984). The following is a description of how [β-Ala$^{28}$]hPACAP(1–38)$NH_2$ was prepared. Other peptides of the present invention can be prepared in an analogous manner by a person of ordinary skill in the art as enabled by the teachings herein.

Preparation of a pharmaceutically-acceptable salt of a peptide of the present invention is well known to those of ordinary skill in the art. For example, the HCl salt of a peptide can be made by dissolving the peptide in water and adding the appropriate of a weak aqueous solution of HCl and then lyophilizing the solution. Other salts may be made in a similar manner or by other methods known to those skilled in the art, such as salt exchange.

EXAMPLE 1

[β-Ala$^{28}$]hPACAP(1–38)$NH_2$

The title peptide was synthesized on an Applied Biosystems (Foster City, Calif.) model 430A peptide synthesizer which was modified to do accelerated Boc-chemistry solid phase peptide synthesis. See Schnoize, et al., Int. J. Peptide Protein Res., 90:180 (1992). 4-Methylbenzhydrylamine (MBHA) resin (Peninsula, Belmont, Calif.) with the substitution of 0.93 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)-OH, Boc-Val-OH, Boc-Leu-OH, Boc-Gly-OH, Boc-Gln-OH, Boc-Ile-OH, Boc-Lys (2CIZ)-OH, Boc-Thr(Bzl)-OH, Boc-Ser(Bzl)-OH; Boc-Phe-OH, Boc-Met-OH and Boc-β-Ala-OH. The synthesis was carried out on a 0.14 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. The partially-deprotected peptide-resin was washed with DMF and DCM and dried under reduced pressure. The final cleavage was done by stirring the peptide-resin in 10 mL of HF containing 1 mL of anisole and dithiothreitol (24 mg) at 0° C. for 75 min. HF was removed by a flow of nitrogen. The residue was washed with ether (6×10 mL) and extracted with 4N HOAc (6×10 mL).

The peptide mixture in the aqueous extract was purified on a reverse-phase preparative high pressure liquid chromatography (HPLC) using a reverse phase Vydac™ $C_{18}$ column (Nest Group, Southborough, Mass.). The column was eluted with a linear gradient (10% to 45% of solution B over 130 min.) at a flow rate of 10 mL/min (Solution A=water containing 0.1% TFA; Solution B=acetonitrile containing 0.1% of TFA). Fractions were collected and checked on analytical HPLC. Those containing pure product were combined and lyophilized to dryness. 286 mg of a white solid was obtained. Purity was >99% based on analytical HPLC analysis. Electro-spray mass spectrometer analysis gave the molecular weight at 4548.5 (in agreement with the calculated molecular weight of 4548.4).

The synthesis of other analogues of the present invention were carried out in the same manner as described for the synthesis of [β-Ala$^{28}$]hPACAP(1–38)NH$_2$ above but using the appropriate protected amino acids.

The protected amino acid 1-[N-tert-butoxycarbonyl-amino]-1-cyclohexane-carboxylic acid (Boc-A6c-OH) was synthesized as follows. 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 mL of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). The two organic layers were combined and washed with water (2×150 ml), dried over anhydrous MgSO$_4$, filtered, and concentrated to dryness under reduced pressure. The residue was recrystallized in ethyl acetate/hexanes. 9.2 g of the pure product was obtained. 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a PACAP analogue of this invention containing A5c, A6c and/or Aib, the coupling time was 2 hrs. for these residues and the immediate residue following them.

The full names for the abbreviations used above are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2CIZ for 2-chlorobenzyloxycarbonyl, 2BrZ for 2-bromobenzyloxycarbonyl and OcHex for O-cyclohexyl.

The substituents $R^1$ and $R^2$ of the above generic formula may be attached to the free amine of the N-terminal amino acid by standard methods known in the art. For example, alkyl groups, e.g., ($C_1$–$C_{30}$)alkyl, may be attached using reductive alkylation. Hydroxyalkyl groups, e.g., $C_{1-12}$ hydroxyalkyl, may also be attached using reductive alkylation wherein the free hydroxy group is protected with a t-butyl ester. Acyl groups, e.g., COX$^1$, may be attached by coupling the free acid, e.g., X$^1$COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

EXAMPLES 2–29

Examples 2–30 were synthesized according to the method described in Example 1 using the appropriately protected amino acid.

| Example | Formula | Mass Spec.* | Calculated M.W. |
|---|---|---|---|
| 2 | [A6c$^{23,27}$]hPACAP(1–38)NH$_2$ | 4559.2 | 4558.7 |
| 3 | [Aib$^{37}$]hPACAP(1–38)NH$_2$ | 4505.5 | 4505.4 |
| 4 | [A6c$^{17}$]hPACAP(1–38)NH$_2$ | 4527.8 | 4528.3 |
| 5 | [A6c$^{19,23}$]hPACAP(1–38)NH$_2$ | 4571.1 | 4572.4 |
| 6 | [A6c$^{23}$]hPACAP(1–38)NH$_2$ | 4546.4 | 4546.4 |
| 7 | [Aib$^{18}$,A6c$^{23}$]hPACAP(1–38)NH$_2$ | 4560.3 | 4560.4 |
| 8 | [Aib$^{18,25}$,A6c$^{23}$]hPACAP(1–38)NH$_2$ | 4574.8 | 4574.4 |
| 9 | [Aib$^{24}$,A6c$^{27}$]hPACAP(1–38)NH$_2$ | 4560.7 | 4560.4 |
| 10 | [A6c$^{23}$,Aib$^{25}$]hPACAP(1–38)NH$_2$ | 4560.7 | 4560.4 |
| 11 | [A6c$^{27}$]hPACAP(1–38)NH$_2$ | 4547.0 | 4546.4 |
| 12 | [Glu$^{16}$]hPACAP(1–38)NH$_2$ | 4535.2 | 4535.3 |
| 13 | [Glu$^{33}$]hPACAP(1–38)NH$_2$ | 4535.2 | 4535.3 |
| 14 | [Aib$^{24}$,Glu$^{25}$]hPACAP(1–38)NH$_2$ | 4605.6 | 4606.4 |
| 15 | [Glu$^{33}$,A6c$^{35}$]hPACAP(1–38)NH$_2$ | 4561.9 | 4561.4 |
| 16 | [A6c$^{35}$]hPACAP(1–38)NH$_2$ | 4560.4 | 4560.4 |
| 17 | [A6c$^{28}$]hPACAP(1–38)NH$_2$ | 4602.1 | 4602.5 |
| 18 | [A5c$^5$]hPACAP(1–38)NH$_2$ | 4532.3 | 4532.3 |
| 19 | [A5c$^{19}$]hPACAP(1–38)NH$_2$ | 4546.4 | 4546.4 |
| 20 | [A5c$^{19}$,β-Ala$^{28}$]hPACAP(1–38)NH$_2$ | 4559.8 | 4560.4 |
| 21 | [GABA$^{28}$]hPACAP(1–38)NH$_2$ | 4562.3 | 4562.4 |
| 22 | [Leu$^{17}$,A5c$^{19}$]hPACAP(1–38)NH$_2$ | 4528.0 | 4528.3 |
| 23 | [Nle$^{17}$,A5c$^{19}$]hPACAP(1–38)NH$_2$ | 4527.2 | 4528.3 |
| 24 | [A5c$^{18}$]hPACAP(1–38)NH$_2$ | 4573.9 | 4574.4 |
| 25 | [β-Ala$^4$]hPACAP(1–38)NH$_2$ | 4547.3 | 4548.4 |
| 26 | [A6c$^{19}$]hPACAP(1–38)NH$_2$ | 4559.3 | 4560.4 |
| 27 | (Ava$^{28}$]hPACAP(1–38)NH$_2$ | 4575.3 | 4576.4 |
| 28 | [(N-α-octadecanoyl-His)$^1$,A5c$^{19}$]hPACAP(1–38)NH$_2$ | 4812.1 | 4812.8 |
| 29 | [A5c$^{19}$,(Lys-N-ε-octadecanoyl)$^{38}$]hPACAP(1–38)NH$_2$ | 4812.2 | 4812.8 |

*Mass spec was taken on a Finnigan Mat SSQ 7000, Electrospray Ionization Mass Spectrometry

What is claimed is:

1. A peptide of formula (I),

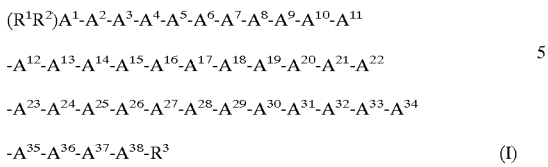

or a pharmaceutically acceptable salt thereof, wherein, $A^1$ is His or Pal;
$A^2$ is Ser, Thr or hSer;
$A^3$ is Asp or Glu;
$A^4$ is Gly, β-Ala, Gaba, Ava, Aib, Acc or HN—$(CH_2)_m$—C(O);
$A^5$ is Ile, Leu, Cha, Nle, Val, Tle, Abu, Aib, Acc or Nva;
$A^6$ is Phe, p-X-Phe, β-Nal, Cha, Tyr, Trp, Acc or Aib;
$A^7$ is Thr, Ser or Val;
$A^8$ is Asp or Glu;
$A^9$ is Ser, Thr or hSer;
$A^{10}$ is Tyr, p-X-Phe, Phe, Amp, β-Nal, Trp or Acc;
$A^{11}$ is Ser, Thr or hSer; $A^{12}$, $A^{14}$ and $A^{15}$ are each independently selected from the group consisting of Arg, Lys, Orn, hArg and HN—CH$((CH_2)_n$—NH—$R^4)$—C—(O);
$A^{13}$ is Tyr, p-X-Phe, Phe, Amp, β-Nal, Trp or Acc;
$A^{16}$ is Gln, Glu, Asp or Asn;
$A^{17}$ is Met, Leu, Nle, Abu, Tle, Val, Ile, Cha, Ala, Aib, Acc or Nva;
$A^{18}$ is Ala, Aib or Acc;
$A^{19}$ is Val, Leu, Ile, Ala, Abu, Tle, Cha, Aib, Acc, Nle or Nva;
$A^{20}$, $A^{21}$, $A^{29}$, $A^{30}$, $A^{32}$, $A^{34}$, $A^{36}$ and $A^{38}$ are each independently selected from the group consisting of Lys, Arg, Orn, hArg and HN—CH$((CH_2)_n$—NH—$R^4)$—C(O) or is deleted;
$A^{22}$ is Tyr, p-X-Phe, Phe, Amp, β-Nal, Trp, Acc or is deleted;
$A^{23}$ is Leu, Ile, Nle, Tle, Met, Val, Ala, Aib, Acc, Cha, Phe, p-X-Phe, Abu, Nva or is deleted;
$A^{24}$ is Ala, Aib, Val, Abu, Acc, Ile, Leu, Nle, Tle, Nva or is deleted;
$A^{25}$ is Ala, Glu, Aib, Val, Abu, Acc, Ile, Leu, Nle, Nva, Tle or is deleted;
$A^{26}$ is Val, Leu, Ile, Ala, Abu, Tle, Cha, Aib, Acc, Nva, Nle or is deleted;
$A^{27}$ is Leu, Ile, Nle, Tle, Met, Val, Ala, Aib, Acc, Nva, Cha, Phe, p-X-Phe, Abu or is deleted;
$A^{28}$ is Gly, Aib, Acc, β-Ala, Gaba, Ava, HN—$(CH_2)_m$—C(O) or is deleted;
$A^{31}$ is Tyr, p-X-Phe, Phe, Amp, β-Nal, Trp, Acc or is deleted;
$A^{33}$ is Gln, Asn, Glu, Asp or is deleted;
$A^{35}$ is Val, Leu, Ile, Ala, Abu, Tle, Cha, Aib, Nva, Acc, Nle or is deleted;
$A^{37}$ is Asn, Gln, Asp, Glu, Ala, Aib, Acc or is deleted;
$R^1$ and $R^2$ are each independently selected from the group consisting of H, $(C_1-C_{30})$alkyl, $(C_2-C_{30})$alkenyl, phenyl-$(C_1-C_{30})$alkyl, naphthyl-$(C_1-C_{30})$alkyl, hydroxy-$(C_1-C_{30})$alkyl, hydroxy$(C_2-C_{30})$alkenyl, hydroxy-phenyl-$(C_1-C_{30})$alkyl or hydroxy-naphthyl-$(C_1-C_{30})$alkyl; or one of $R^1$ or $R^2$ is $COX^2$ where $X^2$ is $(C_1-C_{30})$alkyl, $(C_2-C_{30})$alkenyl, phenyl-$(C_1-C_{30})$alkyl, naphthyl-$(C_1-C_{30})$alkyl, hydroxy-$(C_1-C_{30})$alkyl, hydroxy-$(C_2-C_{30})$alkenyl, hydroxy-phenyl-$(C_1-C_{30})$alkyl or hydroxy-naphthyl-$(C_1-C_{30})$alkyl;

$R^3$ is OH, $NH_2$, $(C_1-C_{30})$alkoxy or NH—Y—$CH_2$—Z, where Y is a $(C_1-C_{30})$ hydrocarbon moiety and Z is $CO_2H$ or $CONH_2$;

where X for each occurrence is independently selected from the group consisting of OH, $OCH_3$, F, Cl, Br and $CH_3$;

m for each occurrence is independently an integer from 5–10;

n for each occurrence is independently an integer from 1–5; and $R^4$ for each occurrence is independently $(C_1-C_{30})$alkyl, $(C_1-C_{30})$acyl or —C((NH)($NH_2$));

provided that the peptide of formula (I) is not:

($R^1R^2$)PACAP(1–27 to 1–38)-X where X is OH or $NH_2$, $R^1$ is H and $R^2$ is H or $(C_1-C_{18})$acyl;

($R^1R^2$)(Nle$^{17}$)PACAP(1–27 to 1–38)-$NH_2$, where $R^1$ is H and $R^2$ is $(C_{10}-C_{18})$acyl;

PACAP(1–23 to 1–26)-X, where X is OH or $NH_2$; or (Y)-PACAP(1–27 to 1–38)-X where X is OH or $NH_2$ and Y is one or more amino acid substitutions selected from the group consisting of Glu$^3$, Glu$^8$, Thr$^{11}$ and Nle$^{17}$.

2. A peptide according to claim 1, wherein at least one of $A^5$, $A^{17}$, $A^{18}$, $A^{19}$, $A^{23}$, $A^{27}$, $A^{28}$ and $A^{35}$ is Acc, or a pharmaceutically acceptable salt thereof.

3. A peptide according to claim 2, wherein at least one of $A^5$, $A^{17}$, $A^{18}$, $A^{19}$, $A^{23}$, $A^{27}$, $A^{28}$ and $A^{35}$ is A6c or A5c, or a pharmaceutically acceptable salt thereof.

4. A peptide according to claim 3, wherein at least one of $A^5$, $A^{18}$ and $A^{19}$ is A5c, or a pharmaceutically acceptable salt thereof.

5. A peptide according to claim 3, wherein at least one of $A^{17}$, $A^{19}$, $A^{23}$, $A^{27}$, $A^{28}$ and $A^{35}$ is A6c, or a pharmaceutically acceptable salt thereof.

6. A peptide according to claim 1, wherein at least one of $A^4$ and $A^{28}$ is β-Ala, Gaba or Ava, or a pharmaceutically acceptable salt thereof.

7. A peptide according to claim 6, wherein at least one of $A^4$ and $A^{28}$ is β-Ala; or a pharmaceutically acceptable salt thereof.

8. A peptide according to claim 6, wherein $A^{28}$ is Gaba or Ava, or a pharmaceutically acceptable salt thereof.

9. A peptide according to claim 1, wherein at least one of $A^{18}$, $A^{24}$, $A^{25}$ and $A^{37}$ is Aib, or a pharmaceutically acceptable salt thereof.

10. A peptide according to claim 1, wherein at least one of $A^{16}$, $A^{25}$ and $A^{33}$ is Glu, or a pharmaceutically acceptable salt thereof.

11. A peptide according to claim 1, wherein $A^{38}$ is Lys-N-ε-octadecanoyl.

12. A peptide according to claim 4, wherein said peptide is [A5c$^5$]hPACAP(1–38)$NH_2$, [A5c$^{19}$]hPACAP(1–38)$NH_2$, [Leu$^{17}$, A5c$^{19}$]hPACAP(1–38)$NH_2$, [Nle$^{17}$, A5c$^{19}$]hPACAP(1–38)$NH_2$, [N-α-octadecanoyl-His$^1$, A5c$^{19}$]hPACAP(1–38)$NH_2$, [A5c$^{19}$, (Lys-N-ε-octadecanoyl)$^{38}$]hPACAP(1–38)$NH_2$ or [A5c$^{18}$]hPACAP(1–38)$NH_2$.

13. A peptide according to claim 5 wherein said peptide is [A6c$^{23,27}$]hPACAP(1–38)$NH_2$, [A6c$^{17}$]hPACAP(1–38)$NH_2$, [A6c$^{19,23}$]hPACAP(1–38)$NH_2$, [A6c$^{23}$]hPACAP(1–38)$NH_2$, [A6c$^{27}$]hPACAP(1–38)$NH_2$, [A6c$^{28}$]hPACAP(1–38)$NH_2$, [A6c$^{35}$]hPACAP(1–38)$NH_2$ or [A6c$^{19}$]hPACAP(1–38)$NH_2$.

14. A peptide according to claim 7, wherein said peptide is [β-Ala ]hPACAP(1–38)NH$_2$, [A5c$^{19}$, β-Ala$^{28}$]hPACAP (1–38)NH$_2$ or [β-Ala$^4$]hPACAP(1–38)NH$_2$.

15. A peptide according to claim 8, wherein said peptide is [Gaba$^{28}$]hPACAP(1–38)NH$_2$ or [Ava 28]hPACAP(1–38) NH$_2$.

16. A peptide according to claim 9, wherein said peptide is [Aib$^{37}$]hPACAP(1–38)NH$_2$, [Aib$^{24}$, A6c$^{27}$]hPACAP (1–38)NH$_2$, [Aib$^{18}$, A6c$^{23}$]hPACAP(1–38)NH$_2$, [Aib$^{18,25}$, A6c$^{23}$]hPACAP(1–38)NH$_2$ or [A6c$^{23}$, Aib$^{25}$]hPACAP (1–38)NH$_2$.

17. A peptide according to claim 10, wherein said peptide is [Glu$^{16}$]hPACAP(1–38)NH$_2$, [Glu$^{33}$]hPACAP(1–38)NH$_2$, [Aib$^{24}$, Glu$^{25}$]hPACAP(1–38)NH$_2$ or [Glu$^{33}$, A6c$^{35}$] hPACAP(1–38)NH$_2$.

18. A pharmaceutical composition comprising an effective amount of a peptide according to claim 1 or a pharmaceutically acceptable salt thereof and a pharmaceutically acceptable carrier.

19. A method of treating cerebrovascular ischemia, male impotence, motor neuron disease, neuropathy, pain, depression, anxiety disorders, brain trauma, memory impairments, dementia, cognitive disorder, central nervous system diseases, migraine, neurodegenerative diseases, ischemic heart disease, myocardial infarction, fibrosis, restenosis, diabetes mellitus, muscle disease, gastric ulcer, stroke, atherosclerosis, hypertension, septic shock, thrombosis, retina disease, cardiovascular disease, renal failure or cardiac failure or preventing neuronal cell death in a mammal in need thereof, which comprises administering to said mammal an effective amount of a peptide according to claim 1 or a pharmaceutically acceptable salt thereof.

20. A method according to claim 19 wherein the central nervous system disease is Parkinson's disease or Alzheimer's disease.

21. A method of binding a PACAP receptor in a mammal in need thereof, which comprises administering to said mammal an effective amount of a peptide according to claim 1 or a pharmaceutically acceptable salt thereof.

22. A method of eliciting an agonist effect from a PACAP receptor in a mammal in need thereof, which comprises administering to said mammal an effective amount of a peptide according to claim 1 or a pharmaceutically acceptable salt thereof.

* * * * *

UNITED STATES PATENT AND TRADEMARK OFFICE
CERTIFICATE OF CORRECTION

PATENT NO. : 6,242,563 B1  Page 1 of 1
DATED : June 5, 2001
INVENTOR(S) : Zheng X. Dung It is certified that error appears in the above-identified patent and that said Letters Patent is hereby corrected as shown below:

Column 17,
Line 2, delete "[β-Ala ]hPACAP(1-38)NH$_2$," insert -- [β-Ala$^{28}$]hPACAP(1-38)NH$_2$, --
Line 5, delete "[Ava 28]hPACAP(1-38)" insert -- [Ava$^{28}$]hPACAP(1-38) --

Signed and Sealed this

Eleventh Day of May, 2004

JON W. DUDAS
*Acting Director of the United States Patent and Trademark Office*